(12) United States Patent
Kipshidze et al.

(10) Patent No.: US 10,993,725 B2
(45) Date of Patent: May 4, 2021

(54) SELECTIVELY DELIVERING PARTICLES INTO THE DISTAL PORTION OF THE LEFT GASTRIC ARTERY

(71) Applicant: Endobar Solutions LLC, Orangeburg, NY (US)

(72) Inventors: Nickolas Kipshidze, New York, NY (US); Ronald J. Solar, San Diego, CA (US)

(73) Assignee: Endobar Sortions LLC, Orangeburg, NY (US)

( * ) Notice: Subject to any disclaimer, the term of this patent is extended or adjusted under 35 U.S.C. 154(b) by 0 days.

(21) Appl. No.: 16/012,303

(22) Filed: Jun. 19, 2018

(65) Prior Publication Data

US 2018/0296225 A1 Oct. 18, 2018

Related U.S. Application Data

(62) Division of application No. 14/740,658, filed on Jun. 16, 2015, now Pat. No. 10,039,551.
(Continued)

(51) Int. Cl.
*A61B 17/12* (2006.01)
*A61M 25/00* (2006.01)
(Continued)

(52) U.S. Cl.
CPC .... *A61B 17/12181* (2013.01); *A61B 17/1204* (2013.01); *A61B 17/12031* (2013.01);
(Continued)

(58) Field of Classification Search
CPC ........ A61B 17/12181; A61B 17/12031; A61B 17/12036; A61B 17/12186;
(Continued)

(56) References Cited

U.S. PATENT DOCUMENTS 5,533,978 A 7/1996 Teirstein
6,435,189 B1* 8/2002 Lewis .................... A61B 17/22
128/898
(Continued)

FOREIGN PATENT DOCUMENTS

JP 2000334047 A 12/2000
JP 2004147916 A 5/2004
WO 2011156348 A1 12/2011

OTHER PUBLICATIONS

International Search Report for corresponding PCT application PCT/US2015/035969, dated Sep. 1, 2015, 13 pages.

*Primary Examiner* — Lauren P Farrar (74) *Attorney, Agent, or Firm* — Potomac Law Group, PLLC (57) ABSTRACT

Methods and apparatuses for embolizing an artery in a living subject using a catheter are disclosed. The catheter has a lumen and also has a balloon located near the distal end of the catheter. The distal end of the catheter is introduced into the artery, and the balloon is inflated to form a seal that prevents blood in the artery from flowing past the balloon. A mixture that includes embolic particles and contrast agent is injected through the lumen into the portion of the artery that is distally beyond the balloon. The subject's own blood or another fluid that contains platelets is injected through the lumen into the portion of the artery that is distally beyond the balloon. Subsequently, the balloon is deflated and the distal end of the catheter is withdrawn.

18 Claims, 9 Drawing Sheets

Related U.S. Application Data (60) Provisional application No. 62/013,062, filed on Jun. 17, 2014.

(51) Int. Cl.
*A61M 25/04* (2006.01)
*A61M 39/22* (2006.01)
*A61M 5/00* (2006.01)
*A61M 25/10* (2013.01)
*A61B 17/00* (2006.01)
*A61B 17/22* (2006.01)
*A61B 90/00* (2016.01)

(52) U.S. Cl.
CPC .. *A61B 17/12036* (2013.01); *A61B 17/12109* (2013.01); *A61B 17/12136* (2013.01); *A61B 17/12186* (2013.01); *A61M 25/0097* (2013.01); *A61M 25/04* (2013.01); *A61B 2017/00818* (2013.01); *A61B 2017/22067* (2013.01); *A61B 2090/3966* (2016.02); *A61M 5/007* (2013.01); *A61M 39/22* (2013.01); *A61M 2025/1052* (2013.01)

(58) Field of Classification Search
CPC .......... A61B 17/1204; A61B 17/12136; A61B 17/12109; A61B 2017/22067; A61B 2017/00818; A61B 2090/3966; A61M 25/04; A61M 25/0097; A61M 2025/1052; A61M 39/22; A61M 5/007
See application file for complete search history.

(56) References Cited

U.S. PATENT DOCUMENTS

| | | |
|---|---|---|
| 6,605,106 B2 | 8/2003 | Schwartz |
| 7,704,220 B2 | 4/2010 | Solar et al. |
| 8,162,879 B2 | 4/2012 | Hattangadi et al. |
| 2003/0078562 A1* | 4/2003 | Makower ......... A61B 17/12136 604/509 |
| 2004/0143225 A1 | 7/2004 | Callan et al. |
| 2011/0282195 A1* | 11/2011 | Solar ................. A61M 25/0026 600/431 |
| 2011/0282382 A1 | 11/2011 | McAlister et al. |
| 2012/0172911 A1 | 7/2012 | Welch |
| 2013/0304107 A1* | 11/2013 | Hassan ........... A61B 17/12136 606/195 |
| 2013/0310687 A1* | 11/2013 | Takizawa ........... A61M 25/104 600/435 |
| 2014/0148757 A1 | 5/2014 | Ambrosina et al. |

* cited by examiner

SELECTIVELY DELIVERING PARTICLES INTO THE DISTAL PORTION OF THE LEFT GASTRIC ARTERY

CROSS REFERENCE TO RELATED APPLICATIONS

This Application is a divisional of U.S. patent application Ser. No. 14/740,658, filed Jun. 16, 2015, which claims the benefit of U.S. Provisional Application 62/013,062, filed Jun. 17, 2014, each of which is incorporated herein by reference.

BACKGROUND

Obesity is widely recognized as a major public health issue resulting in decrease of quality of life and development of chronic diseases, such as metabolic syndrome, diabetes, hypertension, congestive heart failure, atherosclerosis, sleep apnea, etc. Lifestyle changes can be used to treat obesity, but lifestyle changes are not always achievable, especially in long term prospect. Drug therapy is one conventional treatment for obesity, but it is often accompanied by various complications and adverse side effects.

Bariatric surgery is another conventional treatment for obesity. One of the recognized benefits of bariatric surgery is the decreased production of ghrelin. Ghrelin, a neuropeptide which is predominantly produced in the gastric fundus, is the only known hormone that stimulates food intake (orexigenic hormone). It is believed that the decreased production of ghrelin that is associated with bariatric surgery helps promote weight loss. But bariatric surgery is invasive and can be accompanied by considerable surgical complications and/or adverse side effects.

SUMMARY OF THE INVENTION

One aspect of the invention is directed to a method of embolizing an artery in a living subject using a catheter. The catheter has a lumen that provides a fluid tight path between a distal end of the catheter and a proximal portion of the catheter. The catheter also has a balloon located near the distal end of the catheter. This method includes the steps of introducing the distal end of the catheter into the artery, and subsequently inflating the balloon to form a seal that prevents blood in the artery from flowing past the balloon. Subsequently, a first quantity of contrast agent is injected through the lumen into a portion of the artery that is distally beyond the balloon. Based on detected motion of the first quantity of contrast agent, a determination is made whether the balloon has formed an adequate seal. If it is determined that the balloon has not formed an adequate seal an adjustment is made to improve the seal. After the adjustment is made, a mixture that includes embolic particles and a second quantity of contrast agent is injected through the lumen into the portion of the artery that is distally beyond the balloon. A fluid that contains platelets is injected through the lumen into the portion of the artery that is distally beyond the balloon, and this step of injecting the fluid is implemented during or after the step of injecting the mixture. Subsequently, the balloon is deflated. Subsequently the distal end of the catheter is withdrawn.

In some embodiments, the artery is a left gastric artery. In some embodiments, the step of injecting the fluid and the step of injecting the mixture are implemented simultaneously. In some embodiments, the step of injecting the fluid is implemented after the step of injecting the mixture. In some embodiments, the fluid comprises platelet-rich plasma. In some embodiments, the fluid comprises blood, and this blood may optionally be obtained from the subject using an introducer sheath before the blood is injected through the lumen, wherein the introducer sheath is used to guide the catheter during the introducing step. In some embodiments, the method further includes the step of injecting a quantity of blood through the lumen into the portion of the artery that is distally beyond the balloon, and this step is implemented after the step of injecting the first quantity of contrast agent and before the step of injecting the mixture.

In some embodiments, the method further includes the steps of (a) injecting a third quantity of contrast agent through the lumen into the portion of the artery that is distally beyond the balloon, wherein the step of injecting the third quantity of contrast agent is implemented after the introducing step and before the inflating step; (b) determining, based on detected motion of the third quantity of contrast agent, whether the distal end of the catheter is in an appropriate position; and (c) either (i) proceeding to the inflating step if it is determined, in step (b), that the distal end of the catheter is in an appropriate position, or (ii) adjusting the position of the distal end of the catheter if it is determined, in step (b), that the distal end of the catheter is not in an appropriate position.

Another aspect of the invention is directed to a method of embolizing an artery in a living subject using a catheter. The catheter has a lumen that provides a fluid tight path between a distal end of the catheter and a proximal portion of the catheter. The catheter also has a balloon located near the distal end of the catheter. This method includes the steps of introducing the distal end of the catheter into the artery, and subsequently inflating the balloon to form a seal that prevents blood in the artery from flowing past the balloon. Subsequently, a mixture that includes embolic particles and a first quantity of contrast agent is injected through the lumen into the portion of the artery that is distally beyond the balloon. A fluid that contains platelets is injected through the lumen into the portion of the artery that is distally beyond the balloon, and this step of injecting the fluid is implemented during or after the step of injecting the mixture. Subsequently, the balloon is deflated. Subsequently the distal end of the catheter is withdrawn.

In some embodiments, the artery is a left gastric artery. In some embodiments, the step of injecting the fluid and the step of injecting the mixture are implemented simultaneously. In some embodiments, the step of injecting the fluid is implemented after the step of injecting the mixture. In some embodiments, the fluid comprises platelet-rich plasma. In some embodiments, the fluid comprises blood, and this blood may optionally be obtained from the subject using an introducer sheath before the blood is injected through the lumen, wherein the introducer sheath is used to guide the catheter during the introducing step.

In some embodiments, the method further includes the steps of (a) injecting a second quantity of contrast agent through the lumen into the portion of the artery that is distally beyond the balloon, wherein the step of injecting the second quantity of contrast agent is implemented after the introducing step and before the inflating step; (b) determining, based on detected motion of the second quantity of contrast agent, whether the distal end of the catheter is in an appropriate position; and (c) either (i) proceeding to the inflating step if it is determined, in step (b), that the distal end of the catheter is in an appropriate position, or (ii) adjusting the position of the distal end of the catheter if it is determined, in step (b), that the distal end of the catheter is not in an appropriate position.

Another aspect of the invention is directed to an apparatus for embolizing an artery in a living subject. This apparatus includes a catheter having a lumen that provides a fluid tight path between a distal end of the catheter and a proximal portion of the catheter, and a balloon disposed near the distal end of the catheter. The balloon is configured to alternately (a) allow blood to flow through the artery outside the catheter when the balloon is in a deflated state or (b) prevent blood from flowing through the artery outside the catheter when the balloon is in an inflated state. The apparatus also includes a fluid tight chamber having an inflow port, an outflow port, and at least one port for receiving contrast agent and embolic beads. The outflow port is fluidly coupled to the lumen at the proximal portion of the catheter. The apparatus also includes a first valve configured to selectively open or close the inflow port, a second valve configured to selectively open or close the outflow port, and at least one third valve configured to selectively open or close the at least one port for receiving contrast agent and embolic beads. The first valve, the second valve, and the at least one third valve are configured to open an close in a sequence to (a) input embolic particles and a first quantity of contrast agent via the at least one port for receiving contrast agent and embolic beads; (b) inject a mixture that includes the embolic particles and the first quantity of contrast agent through the lumen via the outflow port, (c) input a fluid that contains platelets via the inflow port, and (d) inject the fluid that contains platelets through the lumen via the outflow port.

In some embodiments, the at least one port for receiving contrast agent and embolic beads is implemented as a single port through which both contrast agent and embolic beads travel, and wherein the at least one third valve is implemented using a single valve. In other embodiments, the at least one port for receiving contrast agent and embolic beads is implemented as first port through which the contrast agent travels and a second port through which the embolic beads travel, and wherein the at least one third valve is implemented using separate valves for the contrast agent and embolic beads, respectively. In some embodiments, the apparatus also includes an introducer sheath configured to extract blood from the subject, and blood obtained using the introducer sheath is used as the fluid that contains platelets. The introducer sheath is configured to guide the catheter during introduction of the catheter.

DETAILED DESCRIPTION OF THE PREFERRED EMBODIMENTS

Percutaneous endovascular modification of the function of the gastric fundus using particulate embolization of the distal portion of the left gastric artery is less invasive and more cost effective alternative to bariatric surgery for achieving weight loss.

This application describes a novel approach which involves modifying the arterial blood flow to the gastric fundus by means of percutaneous endovascular flow reduction (or interruption) in the distal portion of the left gastric artery. Experiments in humans (performed outside the U.S.) has demonstrated dramatic weight loss at one month after procedure and sustained for six months follow-up with no reported adverse effects. While reduction in the hunger-mediating peptide hormone ghrelin (secreted in the gastric fundus) has been identified as a one of possible mechanism, the complete physiologic mechanism is not yet clear and may well involve other hormones and/or changes in gastric motility with consequent reduction in hunger sensation in experimental subjects.

The approach described herein achieves endovascular flow reduction or interruption by introducing a plurality of particles into the distal portion of the subject's left gastric artery. The particles, also referred to herein as microparticles, preferably have sizes between 300 and 500 μm, and are delivered via a microcatheter. The particles are preferably compressible and spherical. They are preferably made of polyvinyl alcohol, and more preferably made of acrylamido polyvinyl alcohol. One suitable commercially available product for this purpose is BeadBlock Embolic Beads, 300-500 μm compressible microspheres (Biocompatibles UK Limited, Surrey, UK).

Alternative commercially available products for this purpose include polyvinyl alcohol (PVA foam embolization particles, Cook Medical, Bloomington, Ind.); hydrogel core with Polyzene-F coating (Embozene™ microspheres, CeloNova Biosciences, Inc., San Antonio, Tex.); microspheres made from trisacryl cross linked with gelatin (Embosphere microspheres, Merit Medical Systems, Inc., South Jordan, Utah); HepaSphere™ Microspheres, which are made from two monomers (vinyl acetate and methyl acrylate) that combine to form a copolymer (sodium acrylate alcohol copolymer); Bearing™ nsPVA Embolization Particles, which are irregularly-shaped, biocompatible, hydrophilic, nonresorbable particles produced from polyvinyl alcohol; EmboGold™ Microspheres, which are made from trisacryl cross linked with gelatin and impregnated with 2% elemental gold for visibility; QuadraSphere™ Microspheres, which are also made from two monomers (vinyl acetate and methyl acrylate) that combine to form a copolymer (sodium acrylate alcohol copolymer), and Terumo Bead BlockT microspheres. In alternative embodiments, other embolization materials may be used, including but not limited to coils, other microparticles, foams, different synthetic or organic gels, thrombin, fibrin, collagen, fibrinogen (liquid or powder), and any other material that can occlude blood vessel.

Optionally, certain substances may be added to the particles (or to the other embolization materials) to enhance the effect of the procedure. Examples include, but are not limited to: pharmaceuticals, genetic materials, or different types of cells that also help to decrease production of ghrelin and/or other hormones or other substances that effect appetite in humans.

Figure 1:
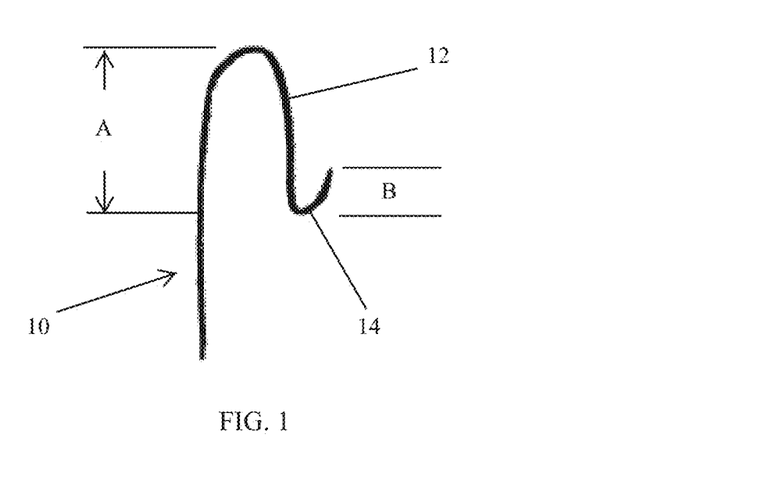
FIG. 1 depicts an example of a suitable shape for the distal end of a custom-shaped guiding catheter with an S-shaped bend.

The procedure involves inserting a catheter into the left gastric artery, which is the major vessel that supplies gastric fundus and modify blood flow. One way to accomplish this is to insert a guiding catheter via the femoral artery or radial artery until the left gastric artery is engaged (in other words, until the distal end of the guiding catheter is introduced into the subject's left gastric artery.) Although the inventor is not aware of any guiding catheters that are specially designed to engage the left gastric artery, examples of suitable guiding catheters for this step include catheters that are already available for other applications such as for coronary angiography and or coronary stenting. In one preferred embodiment, the guiding catheter is a 6 French Heartrail II JR-4.0 guiding catheter (Terumo Europe N.V., Leuven, Belgium). That particular guiding catheter is a Judkins Right type catheter and has a JR-4.0 shape code. In alternative embodiments, a custom-shaped guiding catheter may be used for obtaining easy access to left gastric artery. An example of one suitable shape for such a guiding catheter is provided in FIG. 1, in which the distal end 12 of the custom-shaped guiding catheter 10 has an S-shaped bend. This shape is similar to the shape of the Surefire Axis Catheter (Surefire Medical Inc., Westminster Colo.), but the distal-most bend 14 is increased from about 45° to about 160°. Suitable dimensions for the guiding catheter 10 for accessing the left gastric artery are as follows: A between 3 and 4 inches; and B between ½ and 1 inch.

After the guiding catheter is in position, a microcatheter is then guided through the guiding catheter and introduced into the mid segment or distal portion of the subject's left gastric artery. Once the distal end of the microcatheter has been inserted into the mid segment or distal portion of left gastric artery, the embolization material is delivered into the distal portion of left gastric artery via the microcatheter. The distal shaft of the microcatheter must be small, e.g., 2 French in diameter. One example of a commercially available microcatheter that is suitable for this purpose is the Excelsior 1018 Microcatheter (Boston Scientific Corp., Corck, Ireland).

The presence of the embolization material in the distal portion of left gastric artery will reduce or interrupt the blood flow in the distal portion of left gastric artery, which will modify the blood supply to the fundus of stomach. More specifically, it will reduce or interrupt the blood supply to the fundus.

Using microparticles for the embolization material (as opposed to other types of embolization materials) is advantageous because they are inert, biocompatible, and flow-directed. Moreover, when used as described herein, they will not cause tissue necrosis or unwanted non-target embolization. In contrast, if a chemical-based embolization material such as sodium morrhuate is used instead of the preferred microparticles, deep penetration and or extravasation of this sclerotherapy agent into the gastric tissue may lead to local edema and/or extensive inflammation that results in gastric ulceration and necrosis. Chemical-based embolization material may also lead to systemic toxicity and non-target embolization that may damage the liver, spleen or other organs.

Using particles with sizes between 300 and 500 µm is advantageous because using smaller particles (e.g., 50-100 µm) can result in mucosal necrosis of the fundus, and gastric ulcers. It can also result in non-target embolization of, for example, the esophagus, the liver, and/or the spleen because the small particles can penetrate very deep into tissue and destroy gastric mucosa. Animal experiments have shown that such smaller particles may also end up in structures other than the fundus. In addition, using larger particles (e.g., 700-1000 µm) can result in gastric ulcers, and non-target embolization of, for example, the esophagus, the liver, and/or the spleen. This may be due to deformation of the particles during injections and the formation of larger clusters, which can lead to more proximal embolization. It may also be due to reflux of the particles due to the Venturi effect. In contrast, when particles with sizes between 300 and 500 µm are used, these problems are avoided or at least minimized.

Limiting the delivery of the particles to the distal portion of the subject's left gastric artery is advantageous because when the proximal portion of the left gastric artery is also filled with particles, the risk of esophageal and nonfundus gastric ulcers is very high. More specifically, it was observed in three out of three subjects in animal studies, when tested in pigs. In contrast, these problems were not observed in any of the three pig subjects in which the delivery of the particles was limited to the distal portion of the test subject's left gastric artery.

Thus, by using the correct size of the correct material and delivering it to the correct location, many of the problems associated with other approaches are avoided, and the procedure can be made safe.

EXAMPLE 1

A study was done on five obese subjects to determine the feasibility, safety, and efficacy of embolization of the distal portion of the left gastric artery to reduce plasma ghrelin levels and body weight.

All subjects underwent gastroscopy prior the embolization to assess for the presence of peptic ulcer or gastritis. Gastritis was found in two subjects who subsequently underwent medical treatment. Embolization was performed only after follow-up gastroscopy showed significant improvement in mucosal irritation.

Weights were measured and routine blood samples obtained including a complete blood count, electrolytes, and creatinine prior to embolization.

In the procedure, 6-Fr femoral access was obtained. More specifically, a 6-Fr Heartrail II JR-4.0 guiding catheter (Terumo Europe N.V., Leuven, Belgium) was used to engage the celiac trunk ostium and angiography performed in different projections in order to identify the origin and anatomy of left gastric artery. In some cases, a 0.35" guidewire was advanced into the common hepatic or splenic arteries to stabilize the guiding catheter position.

Figure 5:
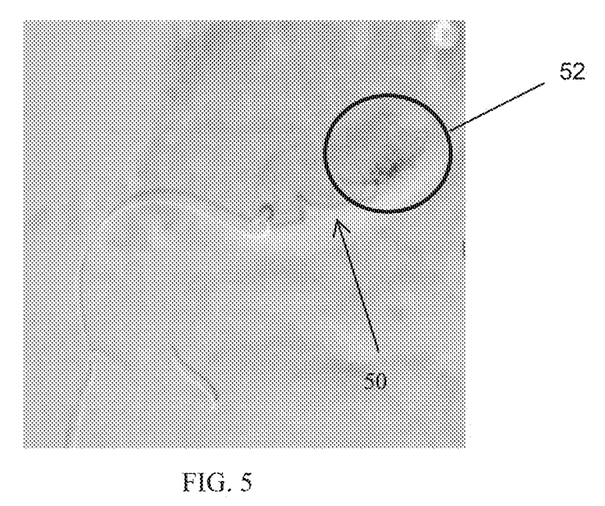
FIG. 5 depicts an angiography of a left gastric artery before the microparticles were delivered to their destination.

The left gastric artery, a branch of the celiac trunk, was wired with a 0.014" Runthrough NS PTCA Guide Wire (Terumo Europe N.V., Leuven, Belgium) and an Excelsior 1018 Microcatheter (Boston Scientific Corp., Corck, Ireland) advanced over the guide wire into the mid segment of the left gastric artery. Subsequently, the guide wire was removed while maintaining the microcatheter position in the left gastric artery and selective angiography performed to ensure proper catheter position and define the anatomy and course of the left gastric artery. FIG. 5 is an angiography of the left gastric artery 50 and the surrounding anatomy after a radio-opaque material was injected into the left gastric artery, but prior to the injection of any particles. The dark artifacts in the circle 52 reveal that blood is flowing in the distal portion of the left gastric artery.

Figure 6:
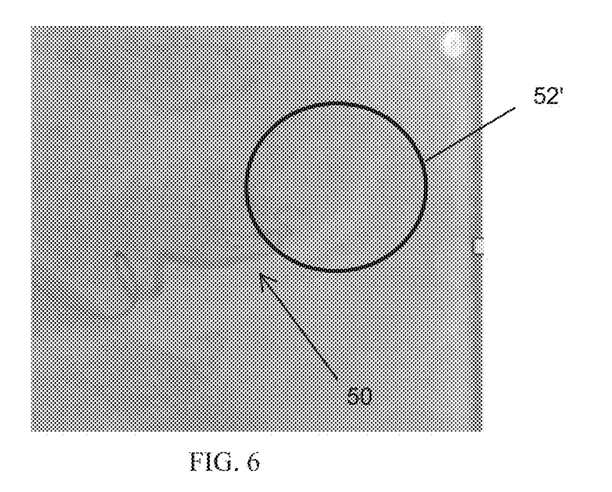
FIG. 6 depicts an angiography of the left gastric artery after the distal portion of that artery was filled with microparticles.

Repeat injections of small amounts of BeadBlock Embolic Bead, 300-500 μm compressible microspheres (Biocompatibles UK Limited, Surrey, UK) mixed with contrast agent (1:1 ratio) were then performed. Angiography was performed between injections of the microspheres to assess left gastric artery flow characteristics. The injection of the microspheres was continued until distal portions of artery branches were no longer visible during radio-opaque contrast injection. This is shown in FIG. 6, which depicts the left gastric artery 50 and the surrounding anatomy. Note the absence of dark artifacts in the circle 52', which indicates that blood is no longer flowing in the distal portion of the left gastric artery.

The guiding and microcatheter were then withdrawn and subjects transferred to a ward, where the introducer sheath was removed and manual pressure applied to obtain hemostasis.

Esophagogastroscopy was performed in all subjects before and after the procedure gastroscopy. A second follow-up gastroscopy was performed one week after the procedure. Weight and fasting plasma ghrelin levels were obtained at baseline and the 1, 3, and 6-month follow-up visits. To obtain the ghrelin levels, clotted blood samples were centrifuged to separate out blood plasma. Fasting levels of ghrelin, ALT, AST, urea and uric acid were then measured. Ghrelin was measured using the Human Ghrelin (TOTAL) RIA KIT (Merck Millipore). Subject's weight and body mass index (BMI) was also calculated at each of the visits.

Figure 2:
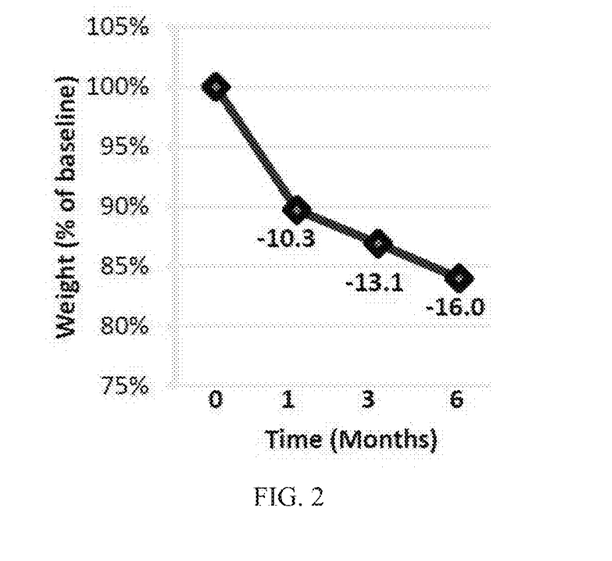
FIG. 2 is a graph that shows how the weight of the subjects changed over time.
Figure 3:
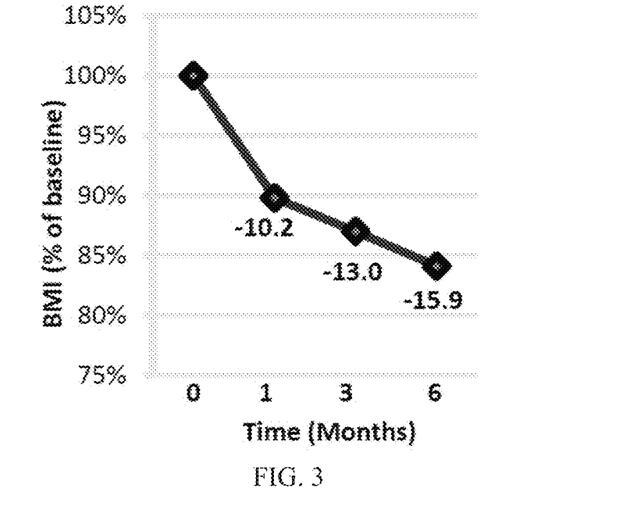
FIG. 3 is a graph that shows how the BMI (body mass index) of the subjects changed over time.
Figure 4:
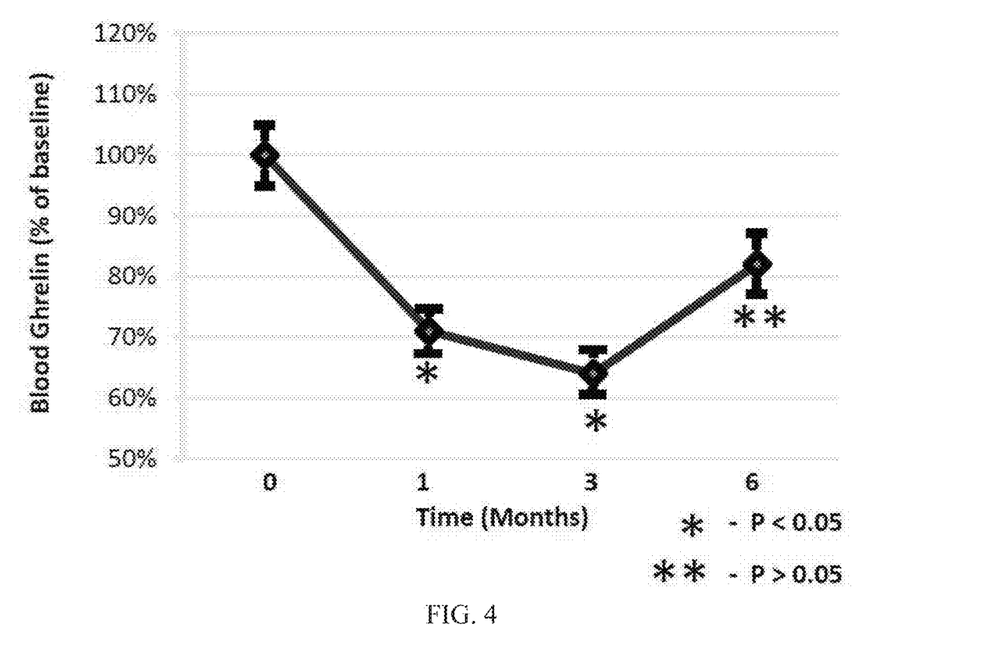
FIG. 4 is a graph that shows how the ghrelin level in the subjects' blood changed over time.

Data for the study is presented below. Table 1 shows the subject data, Table 2 shows the weight at each visit for each subject, Table 3 shows the corresponding BMI, and Table 4 shows the ghrelin levels at each visit for each subject. FIGS. 2, 3, and 4 depict the data in Tables 2, 3, and 4, respectively, in a graphical format.

TABLE 1

| Parameter | Value |
| --- | --- |
| Number of participants | 5 |
| Gender female/male (%) | 20/80% |
| Age female/male (years) | 44.7 ± 7.4 |
| Weight (kg) | 128.1 ± 24.4 |
| BMI (kg/m2) | 42.2 ± 6.8 |
| Ghrelin (pg/ml) | 473.4 ± 189.11 |

TABLE 2

| Subject # | Initial weight (kg) | Weight at 1 month FU | Weight at 3 month FU | Weight at 6 month FU |
| --- | --- | --- | --- | --- |
| 1 | 119 | 102 | 99 | 94 |
| 2 | 165 | 146 | 143 | 140 |
| 3 | 98 | 90 | 85 | 80 |
| 4 | 131 | 120 | 116 | 117 |
| 5 | 127 | 117 | 114 | 107 |
| Mean | 128 ± 24 | 115 ± 21 | 111 ± 22 | 108 ± 23 |
| p Value | | 0.0032 | 0.0012 | 0.0008 |

TABLE 3

| Subject # | Initial BMI | BMI at 1 month FU | BMI at 3 month FU | BMI at 6 month FU |
| --- | --- | --- | --- | --- |
| 1 | 42 | 36 | 35 | |
| 2 | 53 | 47 | 46 | 45 |
| 3 | 34 | 31 | 30 | 28 |
| 4 | 41 | 38 | 37 | 37 |
| 5 | 41 | 38 | 38 | 34 |
| Mean | 42 ± 7 | 38 ± 6 | 37 ± 6 | 36 ± 6 |
| p Value | | 0.0033 | 0.0012 | 0.001 |

TABLE 4

| Subject # | Initial Ghrelin level (pg/ml) | Ghrelin level at 1 month FU | Ghrelin level at 3 month FU | Ghrelin level at 6 month FU |
| --- | --- | --- | --- | --- |
| 1 | 459.6 | 313.4 | 301.3 | 325.5 |
| 2 | 486.1 | 325.9 | 323.6 | 410.9 |
| 3 | 445.5 | 380.7 | 315.8 | 389.1 |
| 4 | 501.2 | 341.6 | 299.7 | 388.6 |
| 5 | 478.3 | 342.2 | 325.5 | 391.3 |
| Mean | 470.54 | 340.76 | 314.18 | 381.08 |
| p Value | | 0.0015 | 0.0002 | 0.0042 |

STATISTICAL ANALYSIS: Statistical analysis was performed using computer software (SPSS 12.0 for Windows, Lead Technologies Inc. 2003. Chicago, Ill.). All values were presented as the mean±standard deviation (±SD). Comparison of weights and plasma ghrelin levels between different time points were done with the paired t-test. A p-value of <0.05 was considered to determine statistical significance RESULTS: There were no procedural complications. Three of the five subjects described mild transient epigastric pain after the procedure. However, follow-up gastroscopies on the day after embolization and at 1-week follow-up did not reveal any abnormalities. All subjects reported a significantly decreased appetite in the first days after the procedure.

Significant progressive weight loss accompanied by reductions in plasma ghrelin levels was observed in all subjects at all follow-ups: Mean weight and BMI was reduced by 10%, 13%, and 16% at 1-, 3- and 6-month follow-up, respectively (Table 2 and 3). Mean initial weight (128.12±24.4 kg) decreased to 108±23 kg (p<0.001). Blood plasma ghrelin levels (initially 473±189) were significantly lower at 1- and 6-month follow-up (by 29% and 36% from baseline, p<0.05) and increased slightly at the 6-month follow-up compared with 3-month follow-up while remaining 18% lower from the baseline (p>0.05).

Figure 7:
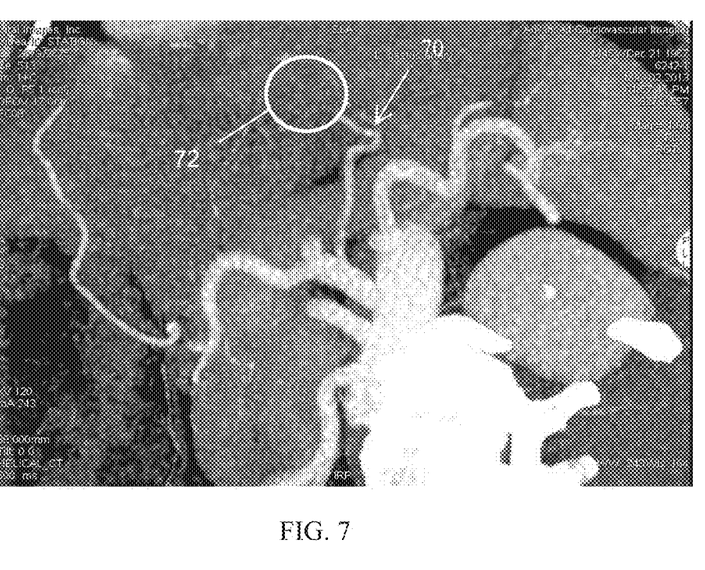
FIG. 7 depicts a CT angiography of the left gastric artery and the surrounding region three months after the distal portion of that left gastric artery was filled with microparticles.

FIG. 7 is a CT angiograph the left gastric artery 70 and the surrounding anatomy that was taken 3 months after procedure. In this figure, portions where blood is flowing are indicated in white. Because the distal portion of the left gastric artery is not visible in region 72, it is apparent that the distal portion remains occluded 3 months after procedure.

The data above demonstrates that embolization of the distal portion of the left gastric artery using microparticles is associated with significant reductions in plasma ghrelin levels and weight loss in humans. It should be noted, however, that after an initial pronounced decline in ghrelin levels after the procedure, the levels did increase at the last follow-up visit (i.e., at the 6 month visit). Although the levels were still lower than the pre-procedure baseline, a long-term study may be warranted to further investigate this increase.

The procedure described above appears to be safe. Specifically, there were no incidences of ulcer formation or injury to remote structures. This may be related to the selective injection into the left gastric artery of beads that are large enough in size as to not allow systemic or remote toxicity, yet small enough to avoid the potential problems described above. Note that with more extensive embolization of arteries other than the left gastric artery, the ulcer risk may be higher. For example, 40% of animals that underwent embolization of the left, short, and accessory gastric arteries developed gastric ulcers in a study by Paxton et al. These ulcers were located at the lesser curvature, suggesting a watershed effect. In addition, using the correct embolic materials as described herein apparently minimizes the extent and likelihood of injury to adjacent or remote tissue.

It should be noted that this example was a non-randomized single-arm feasibility, safety, and efficacy trial with all its inherent limitations. First, the absence of a control group does not allow definitive conclusions regarding efficacy. It is possible that the procedure and study participation led to a higher motivation for diet control and exercise. However, in this case, a decrease in plasma ghrelin levels should not be expected. Second, the intermediate-term follow-up (i.e., 6 months) is too short to make conclusions regarding long-term weight loss, as a rebound phenomenon with recurrent weight gain is conceivable. Third, though not observed in a study by the inventor, a risk of gastric ulcer formation may be significant but too small to have been observed in the study.

Figure 8:
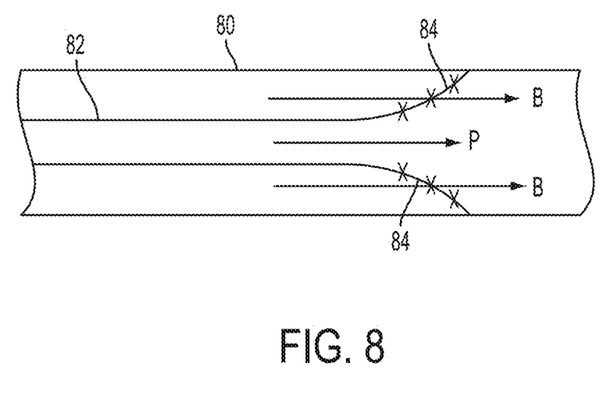
FIG. 8 depicts the distal end of a catheter that may be used to prevent reflux of the microparticles.

Microparticle-based embolization involves clinical risks including gastric ulcer formation, esophageal and liver damage, which may result from non target embolization and consequential retrograde and antegrade reflux of micro particles due to high vascularity of the left gastric artery. In some embodiments, special provisions are made to prevent non target embolization and reflux of the particles, so that they do not travel to other parts of the body. FIG. 8 depicts the distal end of a commercially available catheter (made by Surefire Medical Inc.) that can be used for this purpose. In this embodiment, the wall 82 of the catheter defines an internal lumen, and the particles are delivered through that lumen, as indicated by the arrow labeled P. The distal end 84 of the catheter flares out and preferably touches the inner walls of the artery 80 on all sides of the catheter. At least a portion of the flared distal end 84 is made of mesh, indicated by the "xxx" marking in FIG. 8. The mesh size is selected so that all types of blood components cells can pass (including red blood cells, white blood cells, etc.), but the microparticles cannot pass. A suitable spacing for the mesh for this purpose is between 150 and 250 microns, and preferably about 200 microns. As a result, even though the flared distal end 84 of the catheter touches the walls of the artery 80, blood can still flow as indicated by the arrows B. The flow of blood helps to carry the particles along to their destination in the distal portion of the left gastric artery, and the mesh at the flared distal end 84 prevents the particles from traveling backwards. However, because the left gastric artery has a relatively small diameter, the body of the catheter will block a large portion of the artery, which will reduce the amount of blood that can flow past the catheter. In this embodiment, the blood flow could be reduced to the point where the blood flow will not adequate to direct the particles to their desired destination.

Figure 9:
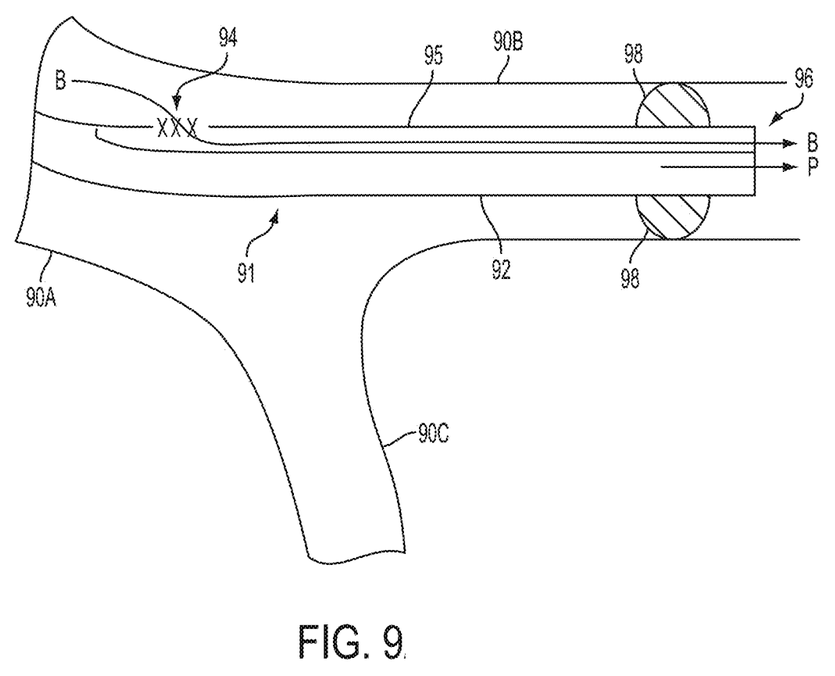
FIG. 9 depicts the distal end of another embodiment of a catheter that is designed to prevent reflux.

FIG. 9 depicts the distal end of a novel catheter that is designed to overcome this problem by maintaining significant blood flow while still preventing reflux of the particles. In this embodiment, the wall 92 of the catheter defines a first internal lumen, and the particles are delivered through that lumen, as indicated by the arrow labeled P. A balloon 98 located at the distal end of the catheter can be inflated in a conventional manner, and the balloon will prevent any particles from refluxing. The balloon 98 is preferably inflated with very low pressure (less than 1 atm), and is preferably designed to fail at low pressure (greater than 2 atm) in order to prevent barotrauma to the blood vessel. The balloon and catheter preferably have a hydrophilic-heparin coating to further minimize vascular trauma.

When the balloon 98 is inflated, there will be no blood flow to help carry the particles along to their destination. To remedy this issue, a second lumen 95 is provided in this embodiment. Blood will enter the second lumen 95 through input port 94 and exit the second lumen 95 through output port 96, as indicated by the arrow labeled B - - - B. Preferably, at least one of the ports 94, 96 is covered with mesh. As in the FIG. 8 embodiment, the mesh size is selected so that all types of blood components cells can pass (including red blood cells, white blood cells, etc.), but the microparticles cannot pass. A suitable spacing for the mesh for this purpose is between 150 and 250 microns, and preferably about 200 microns. Due to the second lumen 95, blood can flow through the artery 90B even though the balloon 98 is inflated. The flow of blood through the second lumen will be sufficient to carry the particles along to their destination in the distal portion of the left gastric artery. In some preferred embodiments, the length of the lumen 95 is long enough so that the input port 94 is disposed in a relatively wide portion of the vasculature, such as the celiac artery 90A (i.e., before the left gastric artery 90B branches off from the splenic and common hepatic arteries, both illustrated schematically as 90C), or even the aorta (not shown). This arrangement will make it even easier for the blood to flow into the input port 94, so that the blood flow can direct the particles to their desired destination.

Figure 10:
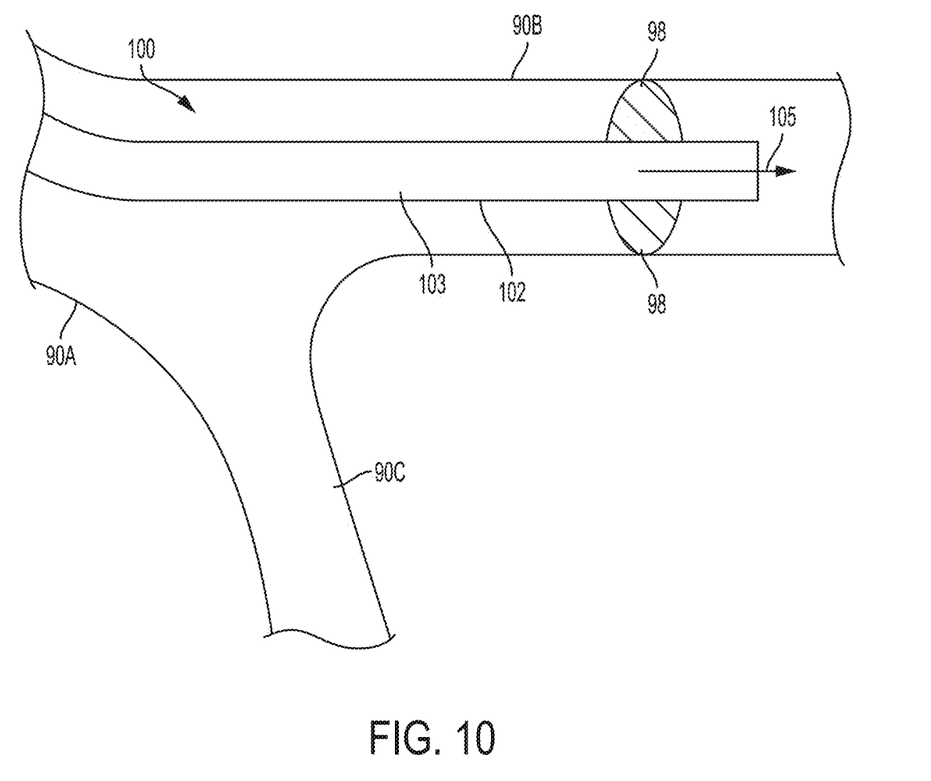
FIG. 10 depicts the distal end of another embodiment of a catheter that is designed to prevent reflux.

FIG. 10 depicts the distal end of another embodiment of a catheter 100 that is designed to prevent reflux of the particles. In this embodiment, the sidewall 102 of the catheter surrounds a main internal lumen 103. Particles and blood are delivered through that main lumen 103 as indicated by the arrow 105. A balloon 98 located near the distal end of the catheter 100 can be inflated in a conventional manner, in which case the balloon will prevent reflux of the particles that are injected via the catheter 100. The balloon is 98 preferably inflated with very low pressure (less than 1 atm), and is preferably designed to fail at low pressure (greater than 2 atm) in order to prevent barotrauma to the blood vessel. The balloon 98 and catheter 100 preferably have a hydrophilic-heparin coating to further minimize vascular trauma. As in the FIG. 9 embodiment, when the balloon 98 is inflated, there will be no bloodflow to help carry the particles along to their destination. To remedy this issue, blood can be extracted from another portion of the patient's body and injected into the proximal end of the main lumen 103.

Figure 11:
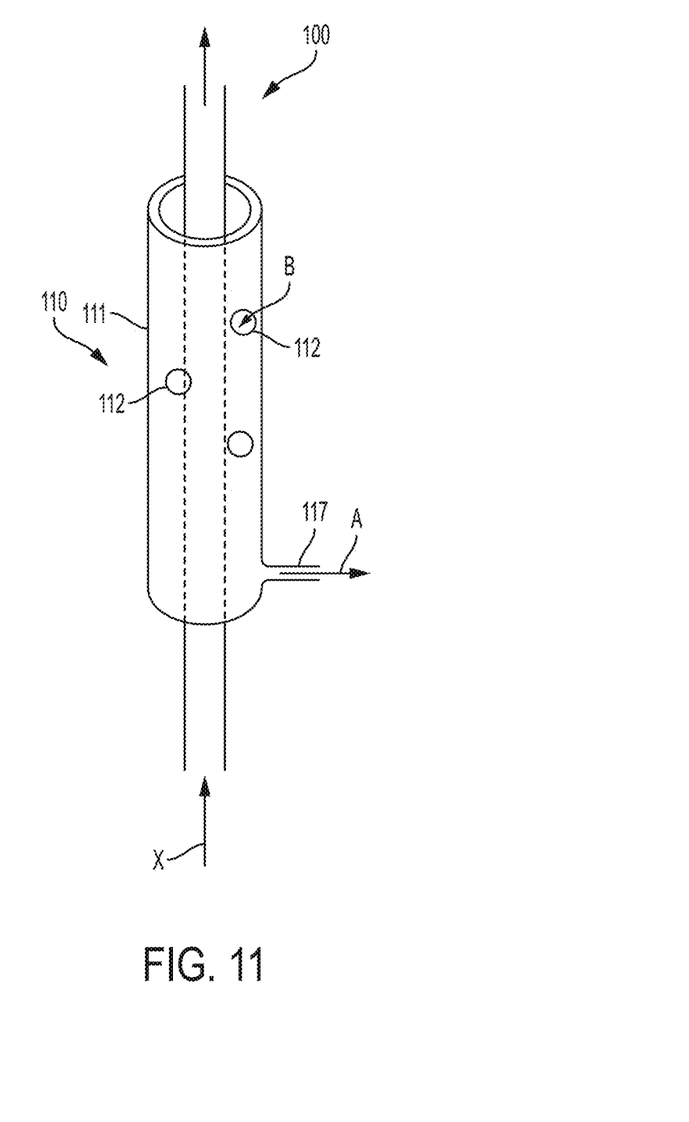
FIG. 11 depicts an introducer sheath for use with the FIG. 10 catheter.

FIG. 11 depicts an introducer sheath 110 that is suitable for extracting blood for this purpose. The introducer sheath has fluid-tight floor and a sidewall 111, preferably with at least one hole 112 disposed therein. When the introducer sheath is positioned at the catheter insertion site, blood from the patient's body can enter the holes 112 and exit the introducer sheath 110 through exit port 117, as indicated by the inflow arrow B and the outflow arrow A. The outflow blood is provided to an extracorporeal device.

Figure 12:
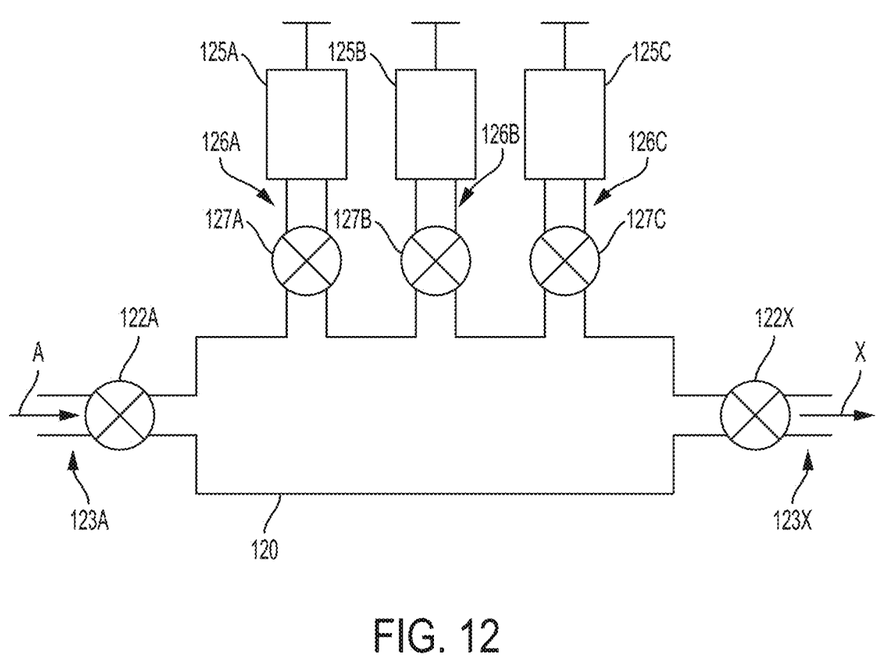
FIG. 12 depicts an exemplary embodiment of an extracorporeal device that is used to orchestrate the flow of all the relevant substances in connection with the FIG. 10 catheter.

In some embodiments, this extracorporeal device is implemented using a simple manifold 120 as depicted in FIG. 12. The manifold 120 is a fluid tight chamber that is provided with inputs and outputs that make it suitable for orchestrating the flow of all the relevant substances so that the particles can be delivered to their intended destination in the left gastric artery.

Appropriate tubing (not shown) is used to connect the exit port 117 of the introducer sheath 110 to the inflow port 123A of the manifold 120. Blood from the exit port 117 of the introducer sheath 110 that arrives at the manifold 120 is depicted by arrow A. Appropriate outflow tubing is also used to connect the outflow port 123X of the manifold 120 to the proximal end of the catheter 100, in fluid communication with the main lumen 103 of the catheter 100. Note that in alternative embodiments, the outflow port 123X of the manifold 120 may be connected directly to the proximal end of catheter 100, instead of connecting those two parts using tubing. The output of the manifold is depicted by arrow X, and that output is routed back to the main lumen 103 of the catheter (depicted in FIG. 11 and FIG. 10) via the outflow tubing. Stopcocks 122A and 122X are provided at the inflow port 123A and outflow port 123X of the manifold, respectively.

The manifold 120 has three stopcocks 127A, 127B, 127C, and three ports 126A, 126B, and 126C that are configured to accept syringes connected at the distal and of each of the stopcocks 127A-C. In FIG. 12, three syringes 125A, 125B, and 125C are depicted as being connected to these ports 126A-C. The description below assumes that all five stopcocks 127A-C, 122A, and 122X start out in the closed position. Note that although the illustrated embodiment uses stopcocks, other types of valves may be used in place of stopcocks to control the flow of the various substances described herein (e.g., blood, contrast agent, particles, etc.).

To use the system, an introducer sheath 110 is installed at an appropriate entry position such as the femoral artery. The introducer sheath 110 facilitates both insertion of the catheter and extraction of blood from the patient's body. A guide wire (not shown) is advanced through the introducer sheath 110 in any conventional manner until the distal end of the guide wire is disposed in the left gastric artery in a conventional manner. The catheter 100 is then introduced over the guide wire in a conventional manner until the distal end of the catheter 100 is in the desired position in the left gastric artery 90B, as shown in FIG. 10. Optionally, the catheter 100 includes a radio opaque marker at or near the distal end to assist positioning. After the catheter has been positioned in its desired location, the guide wire is removed.

An empty syringe 125A is then connected to port 126A, and stopcocks 122A and 127A are opened. The plunger on the syringe 125A is withdrawn, which draws blood from the patient into the syringe 125A. The stopcocks 122A and 127A are then closed. At this point, a quantity of blood (e.g., between 1 and 20 cc, or between 5 and 10 cc) is temporarily being stored in the syringe 125A.

Syringe 125B is then filled with an appropriate quantity of contrast agent (e.g., between 1 and 20 cc, or between 5 and 10 cc) and connected to port 126B. The stopcock 127B and 122X are opened and the plunger of the syringe 125B is depressed. Contrast agent will then flow into the manifold 120, out of the outflow port 123X and into the catheter 100. The contrast agent will exit the distal end of the catheter 100 (shown in FIG. 10). This step is used to assist in the correct placement of the distal end of the catheter 100 in a conventional manner.

After it is determined that the distal end of the catheter 100 is in the desired location (using any conventional approach), the balloon 98 is inflated in a conventional manner (e.g., using a fluid or gas that is supplied via an inflation lumen, not shown). Optionally, a second injection of contrast agent may be performed after the balloon inflation to verify that the balloon 98 has adequately sealed off the artery. If the artery is not adequately sealed, appropriate adjustments may be made and one or more additional injections of contrast agent may be made. The stopcock 127B is now closed. Note that it may be necessary to refill the syringe 125B with additional contrast agent if it is needed to implement these steps.

Preferably, after the contrast agent has been injected, the catheter is flushed with all of the blood that was previously stored in the syringe 125A. This can be accomplished by opening the stopcock 127A and fully depressing the plunger of the syringe 125A. Alternatively, syringe 125B may be filled with sterile saline, and the sterile saline may be used to flush the catheter.

At this point in the procedure, the outflow stopcock 122X is closed and the stopcock 127A is opened. If syringe 125B does not contain enough contrast agent to implement the following steps, the syringe 125B should be refilled with additional contrast agent. A syringe 125C containing the embolic particles mixed with a liquid in a conventional manner is now connected to the port 126C and the stopcocks 127B and 127C are open. The plungers on the syringes 125B and 125C are then depressed. This injects the particles from the syringe 125C and the contrast agent from the syringe 125B. The contents of both these syringes will then flow through the manifold 120 and back up into the syringe 125A because both the inflow stopcock 122A and the outflow stopcock 122X are closed at this point. Stopcocks 127B and 127C are then closed and the outflow stopcock 122X is opened. The plunger on the syringe 125A is then depressed, which injects the mixture of particles and contrast agent from the syringe 125A into the manifold 120. Preferably the plunger is depressed at a slow speed. From the manifold 120 the mixture will flow out of the outflow port 123X and through the catheter 100, and will exit the catheter 100 and flow into the distal portion of the left gastric artery 90B (shown in FIG. 10). The outflow stopcock 122X is then closed.

Note that in alternative embodiments, instead of supplying the particles and the contrast agents from separate syringes 125B and 125C, those two components can be premixed into a single syringe 125C, and injected directly from that single syringe 125C into the manifold 120, after which the path of the mixture will continue as indicated above.

After the particles have been delivered to their intended destination in the left gastric artery, it is preferable to deliver a quantity of blood (e.g., 1-5 cc) to the left gastric artery to help carry the particles to their destination in the artery, and so that the blood can interact with the particles, which will help block the flow of blood to more distal portions of the left gastric artery. To accomplish this, stopcock 127A and the inflow stopcock 122A is opened and the plunger of the syringe 125A is withdrawn to extract blood from the patient. The inflow stopcock 122A is then closed and the outflow stopcock 122X is opened. The plunger on the syringe 125A is then depressed, which pumps the blood from the syringe 125A through the manifold 120 and the catheter 100 and delivers the blood to the left gastric artery. Preferably the plunger is depressed at a slow speed. In alternative embodiments, instead of injecting the blood after the mixture of particles and contrast agent has been injected, a quantity of blood can be mixed in with the particles and the contrast agent, and all three of those components can be injected simultaneously.

Use of the patient's own blood as described above preferred. The flow of the patient's own blood will mimic the patient's own native circulation to help carry the particles to their intended destination. In alternative embodiments, a different fluid that contains platelets (e.g., platelet-rich plasma) may be used instead of whole blood to interact with the particles. The platelets in the fluid will interact with the particles to (e.g., by forming a thrombosis) to help block the flow of blood to more distal portions of the left gastric artery.

All the stopcocks are then closed, the balloon 98 (depicted in FIG. 10) is deflated, the system is detached, and the catheter 100 is withdrawn. In some embodiments, a small barrel syringe (1-3 cc) is used to implement the syringe 125A, to facilitate the injections of blood and the bead/contrast mixture. This variety of syringe is advantageous since the force required to push the plunger will be reduced. However, due to the small volume of this variety of syringe, the steps to fill syringe 125A may require repetition in order to inject the desired volumes of the relevant substances.

Blood pressure is preferably monitored before, during, and after the procedures described above. Note that while FIG. 12 depicts a manual device for implementing the procedure described above, in alternative embodiments, the manifold 120 can be replaced with other extracorporeal devices, including but not limited to an automated system (not shown) with suitable valves and pumps configured to implement similar functionality as the manifold 120 and syringes 125A-C described above.

The technique of active delivery of blood described above in connection with FIGS. 10-12 may be more advantageous than relying on passive blood flow (as described above in connection with FIG. 9). This is because passive flow may be restricted or otherwise affected, by physiological circumstances, such as vasoconstriction and changes in blood pressure, which may go unnoticed. On the other hand, by using the embodiment of FIGS. 10-12, the physician can control the active delivery of blood, and adequate blood flow can help improve embolization and increase the of number of particles delivered to target area. Also, with active delivery, the blood may be delivered in precise sequences, which may improve targeting of the embolization.

Note also that the methods and apparatus described above in connection with FIGS. 10-12 may also be used with different embolization materials, including but not limited to onyx, fibrin glue, and radioactive beads.

The FIG. 10-12 embodiment described above is designed for controlled, safe, targeted delivery of embolic agents using VLP balloon occlusion with controlled expansion to minimize barotrauma and autoperfusion capability for sequential blood infusion to enhance targeted embolization and ability to measure pressure to control delivery of particles.

Two studies were done to test the FIG. 10-12 embodiment. Pigs were chosen for these studies because of the anatomical similarities with a human's organs (e.g., gastric fundus, and gastric and peripheral arteries). Moreover, a pig's vasculature is accessible with conventional equipment, such as a diagnostic and guiding catheters, which allowed for the evaluation of pigs arteries by angiography and results of embolization. Gross anatomical analysis was performed in both studies to evaluate overall tissue architecture, ulcerations, damage or infarction to different organs.

One study was implemented in the kidneys, liver, and spleen of two pigs, using both the FIG. 10-12 embodiment and a conventional Maestro-Merit Medical microcatheter (with no manifold) as a control in different arteries of the relevant organ in each pig. In this study, angiography demonstrated better microparticle penetration with the FIG. 10-12 embodiment, demonstrated by contrast density, complete filling of target segment of kidneys, different segments of liver and spleen and enhanced tissue interaction. The usage of contrast agent and embolic beads was significantly lower for the FIG. 10-12 embodiment versus the control. Additionally, angiography before and during embolization demonstrated no reflux with the FIG. 10-12 embodiment, versus significant retrograde reflux in the control sites.

A second study was implemented as an initial evaluation of safety and efficacy of the FIG. 10-12 embodiment to reduce plasma ghrelin levels and body weight in pigs. In this study, embolization of the left gastric artery of 9 pigs was performed using micro particles (Embo shield, Merit Medical, Salt Lake City, Utah) of 300-500 micrometer size. In six pigs, (two acute and four with a one month follow-up), the embolization was performed using the FIG. 10-12 embodiment. In the remaining three pigs (one acute and two with a one month follow-up), the embolization was performed using a conventional Maestro-Merit Medical microcatheter (with no manifold) as a control. Safety and efficacy was evaluated by angiography, gross anatomy and histology (H&E and Imunno staining) and weight gain in the chronic animals.

The weight and ghrelin level data for the second study were as follows:

TABLE 5

| Subject # | Initial weight (kg) | 1 week (kg) | 2 weeks (kg) | 3 weeks (kg) | 4 weeks (kg) |
| --- | --- | --- | --- | --- | --- |
| Control A | 32.2 | 34.0 | 36.5 | 35.2 | 33.8 |
| Control B | 37.1 | 38.0 | 42.0 | 43.7 | 42.6 |
| 1 | 29.0 | 30.9 | 35.6 | 34.1 | 33.8 |
| 2 | 32.3 | 29.0 | 28.1 | 26.8 | 30.0 |
| 3 | 30.5 | 33.6 | 34.3 | 30.9 | 29.1 |
| 4 | 36.1 | 36.8 | 36.7 | 30.5 | 28.9 |

TABLE 6

| Subject # | Initial ghrelin (pp/ml) | 1 week (pp/ml) | 2 weeks (pp/ml) | 3 weeks (pp/ml) | 4 weeks (pp/ml) |
| --- | --- | --- | --- | --- | --- |
| Control A | 640 | 550 | 576 | 563 | 538 |
| Control B | 589 | 501 | 477 | 495 | 442 |
| 1 | 701 | 580 | 568 | 554 | 533 |
| 2 | 789 | 647 | 592 | 568 | 537 |
| 3 | 631 | 473 | 504 | 454 | ??? |
| 4 | 680 | 530 | 496 | 414 | 442 |

Atraumatic navigation of small tortuous vessels for LGA embolization was achieved with the FIG. 10-12 embodiment. There was better bead penetration with FIG. 10-12 embodiment versus the control demonstrated by contrast density, with complete filling of target segment. The FIG. 10-12 embodiment also required less contrast agent and embolic beads than the control. Angiography of the left gastric artery demonstrated no reflux in all six pigs for the FIG. 10-12 embodiment, versus significant retrograde and antegrade reflux in all 3 control animals. Gross anatomy revealed targeted embolization of the gastric fundus with the FIG. 10-12 embodiment, versus damage of esophagus, liver and gastric pylorus and body in all three control animals.

The second study also quantitatively measures the Ghrelin positive population in the fundus, body and pyloric regions of the stomach by immunohistochemistry and histomorphometry. Twelve tissue sections from the fundus, two tissue sections from the body and two tissue sections from the pyloric regions were taken for routine paraffin embedding and sectioning. Four-micron histologic sections were stained with routine H&E stain and immunohistochemical stain for Ghrelin (Ghrelin [Porcine] antibody for IHC, catalog #H-031-52. Phoenix Pharmaceuticals, Inc, 330 Beach Road, Burlingame, Calif. 94010, USA (800) 988-1205) at 1:2000 dilution. These slides are scanned with a whole-slide scanner using the 20X objective (Aperio ScanScope System, Aperio Technologies, Inc. 1360 Park Center Drive, Vista, Calif. 92081 866-478-4111). Using the Aperio ScanScope software with the Genie and the nuclear algorithms we measured the mucosal area and the number of brown staining Ghrelin positive cells. The algorithm was validated against the manual count with an average discrepancy of 3.05% excluding the three histologic section outliers.

This testing revealed that the FIG. 10-12 embodiment resulted in significantly fewer Ghrelin Positive Cells Cells/MM2 in the fundus versus the control, as indicated in the table below.

TABLE 7

Ghrelin cells in fundus of stomach after embolization

| | Area of Mucosa (mm$^2$) | Number of Ghrelin Positive Cells | Ghrelin Positive Cells per mm$^2$ |
|---|---|---|---|
| FIG. 10-12 embodiment (n = 4) | 10.11 ± 14.17 | 310.88 ± 360.23 | 23.63 ± 14.86 |
| Control (n = 2) | 21.75 ± 8.23 | 512.77 ± 345.94 | 57.26 ± 19.11 |

CONCLUSIONS: Percutaneous embolization of the distal portion of the left gastric artery with embolic beads as described in the study is feasible and appears to be safe. It leads to a reduction in plasma ghrelin levels and is accompanied by a significant weight loss at intermediate term follow-up. It may be a good tool to enhance weight loss in subjects with morbid obesity who cannot achieve weight loss by conventional means (diet and exercise) and an alternative to or complimentary to bariatric surgery.

Note that while the embodiments described above are described in the context of the left gastric artery and the fundus of the stomach, similar techniques may be used in other arteries to embolize different portions of a patient's anatomy. Examples include, but are not limited to, portions of the stomach that are adjacent to the right gastric artery, the short gastric artery, the gastro-epiploic artery, the right gastro-omental artery, the left gastro-omental artery, or any branches thereof. In these alternative anatomic regions, the same apparatus and methods described above may be used. Alternatively, appropriate modifications may be made to optimize the apparatus and methods to other portions of the anatomy.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of embolizing an artery in a living subject using a catheter, the catheter having a lumen that provides a fluid tight path between a distal end of the catheter and a proximal portion of the catheter and a balloon located near the distal end of the catheter, the method comprising the steps of:
   introducing the distal end of the catheter into the artery;
   inflating the balloon to form a seal that prevents blood in the artery from flowing past the balloon, wherein the inflating step is implemented after the introducing step;
   injecting a first quantity of contrast agent through the lumen into a portion of the artery that is distally beyond the balloon, wherein the step of injecting the first quantity of contrast agent is implemented after the step of inflating the balloon;
   determining, based on detected motion of the first quantity of contrast agent, whether the balloon has formed an adequate seal;
   making an adjustment to improve the seal if it is determined, in the determining step, that the balloon has not formed an adequate seal;
   injecting a mixture that includes embolic particles and a second quantity of contrast agent through the lumen into the portion of the artery that is distally beyond the balloon, wherein the step of injecting the mixture is implemented after the step of making an adjustment;
   injecting a fluid that contains platelets through the lumen into the portion of the artery that is distally beyond the balloon, wherein the step of injecting the fluid is implemented during or after the step of injecting the mixture;
   deflating the balloon, wherein the deflating step is implemented after the step of injecting the fluid; and
   withdrawing the distal end of the catheter, wherein the withdrawing step is implemented after the deflating step.

2. The method of claim 1, wherein the artery is a left gastric artery.

3. The method of claim 1, wherein the step of injecting the fluid and the step of injecting the mixture are implemented simultaneously.

4. The method of claim 1, wherein the step of injecting the fluid is implemented after the step of injecting the mixture.

5. The method of claim 1, wherein the fluid comprises platelet-rich plasma.

6. The method of claim 1, wherein the fluid comprises blood.

7. The method of claim 6, wherein the blood is obtained from the subject using an introducer sheath before the blood is injected through the lumen, and wherein the introducer sheath is used to guide the catheter during the introducing step.

8. The method of claim 1, further comprising the step of injecting a quantity of blood through the lumen into the portion of the artery that is distally beyond the balloon, wherein the step of injecting the quantity of blood is implemented after the step of injecting the first quantity of contrast agent and before the step of injecting the mixture.

9. The method of claim 1, further comprising the steps of:
   (a) injecting a third quantity of contrast agent through the lumen into the portion of the artery that is distally beyond the balloon, wherein the step of injecting the third quantity of contrast agent is implemented after the introducing step and before the inflating step;

(b) determining, based on detected motion of the third quantity of contrast agent, whether the distal end of the catheter is in an appropriate position; and (c) either (i) proceeding to the inflating step if it is determined, in step (b), that the distal end of the catheter is in an appropriate position, or (ii) adjusting the position of the distal end of the catheter if it is determined, in step (b), that the distal end of the catheter is not in an appropriate position.

10. A method of embolizing an artery in a living subject using a catheter, the catheter having a lumen that provides a fluid tight path between a distal end of the catheter and a proximal portion of the catheter and a balloon located near the distal end of the catheter, the method comprising the steps of:

introducing the distal end of the catheter into the artery;

inflating the balloon to form a seal that prevents blood in the artery from flowing past the balloon, wherein the inflating step is implemented after the introducing step;

injecting a mixture that includes embolic particles and a first quantity of contrast agent through the lumen into a portion of the artery that is distally beyond the balloon, wherein the step of injecting the mixture is implemented after the inflating step;

injecting a fluid that contains platelets through the lumen into the portion of the artery that is distally beyond the balloon, wherein the step of injecting the fluid is implemented during or after the step of injecting the mixture;

deflating the balloon, wherein the deflating step is implemented after the step of injecting the fluid; and withdrawing the catheter, wherein the withdrawing step is implemented after the deflating step.

11. The method of claim 10, wherein the artery is a left gastric artery.

12. The method of claim 10, wherein the step of injecting the fluid and the step of injecting the mixture are implemented simultaneously.

13. The method of claim 10, wherein the step of injecting the fluid is implemented after the step of injecting the mixture.

14. The method of claim 10, wherein the fluid comprises platelet-rich plasma.

15. The method of claim 10, wherein the fluid comprises blood.

16. The method of claim 15, wherein the blood is obtained from the subject using an introducer sheath before the blood is injected through the lumen, and wherein the introducer sheath is used to guide the catheter during the introducing step.

17. The method of claim 10, further comprising the steps of:

(a) injecting a second quantity of contrast agent through the lumen into the portion of the artery that is distally beyond the balloon, wherein the step of injecting the second quantity of contrast agent is implemented after the introducing step and before the inflating step;

(b) determining, based on detected motion of the second quantity of contrast agent, whether the distal end of the catheter is in an appropriate position; and (c) either (i) proceeding to the inflating step if it is determined, in step (b), that the distal end of the catheter is in an appropriate position, or (ii) adjusting the position of the distal end of the catheter if it is determined, in step (b), that the distal end of the catheter is not in an appropriate position.

18. The method of claim 10, wherein the embolic particles are between 300 and 500 μm in size.

* * * * *